US00PP32895P3

(12) United States Plant Patent
Dal Pane

(10) Patent No.: US PP32,895 P3
(45) Date of Patent: Mar. 16, 2021

(54) KIWI PLANT NAMED 'RED QUEEN'

(50) Latin Name: ***Actinidia chinensis* Planch**
Varietal Denomination: Red Queen

(71) Applicant: Red Kiwi S.r.l., Riolo Terme (IT)

(72) Inventor: Maurizio Dal Pane, Castel Bolognese (IT)

(73) Assignee: Red Kiwi S.r.l., Riolo Terme (IT)

( * ) Notice: Subject to any disclaimer, the term of this patent is extended or adjusted under 35 U.S.C. 154(b) by 0 days.

(21) Appl. No.: 16/602,394

(22) Filed: Sep. 27, 2019

(65) Prior Publication Data

US 2020/0296871 P1 Sep. 17, 2020

(30) Foreign Application Priority Data

Mar. 11, 2019 (QZ) ..... PBR 20190516

(51) Int. Cl.
*A01H 5/08* (2018.01)
*A01H 6/00* (2018.01)

(52) U.S. Cl.
USPC ..... Plt./156
CPC ..... *A01H 6/00* (2018.05); *A01H 5/08* (2013.01)

(58) Field of Classification Search
USPC ..... Plt./156
CPC ..... A01H 5/08
See application file for complete search history.

*Primary Examiner* — Kent L Bell
(74) *Attorney, Agent, or Firm* — Lowe Graham Jones PLLC

(57) ABSTRACT

A new and distinct kiwi plant of the species *Actinidia chinensis* is described. The cultivar results from a controlled pollination using a female *A. chinensis* selection RS1 and a male selection (Tomuri and Chieftain). Named parents (RS1, Tomuri and Chieftain) are believed to be unpatented cultivars in the United States. The new cultivar is distinguished by its medium fruit size, ovoid fruit shape, general hairlessness, greenish-brown fruit coloring, and its harvest date in mid-October in Italy.

7 Drawing Sheets

FIELD OF THE INVENTION

Genus and species of plant claimed: *Actinidia chinensis* Planch.

PRIORITY CLAIM

The present application claims priority from Community Plant Variety Office (European Union) Application No. 20190516, filed Mar. 11, 2019, which is herein incorporated in its entirety by reference.

BACKGROUND OF THE INVENTION

Kiwi plants in cultivation are mainly varieties of *A. deliciosa*, although some *A. chinensis* and *A. arguta* varieties are grown. *A. deliciosa* and *A. chinensis* are closely related and varieties of both types have large fruit (about 100 g) with hair on the skin. Main varieties of Kiwi plants include 'Hayward' (*A. deliciosa*) and 'Hort16A' (*A. chinensis*). 'Hayward' is not patented, while 'Hort16A' is subject to U.S. Plant Pat. No. 11,066. All *Actinidia* species are dioecious, so female varieties have to be interplanted with male pollinizers to ensure fruit production. Fruit are usually cut and eaten with a spoon. 'Tomuri' and 'Chieftain' are both esaploid males which are commonly used to pollinate esaploid varieties such as 'Hayward', and also 'RS1'. As they are both not synchronized with Red varieties, which bloom much earlier than 'Tomuri' and 'Chieftain' so male pollen has to be collected from male vines one year in advance, and then distributed on females during blooming, either dry (mixed with lycopodium) or in a liquid solution.

'RS1' is a red kiwifruit variety which germinates in Northern Italy around 15 days before 'Hayward' (means around 3$^{rd}$ week of March) and blooms 15 days before 'Hayward' (means around April 20$^{th}$). It is a medium vigorous plant with short interno-knots. It adapts to a wide range of climates, but barely stand temperatures below 0° C. cause of its high sensitiveness to *Pseudomonas syringae* pv. *actinidiae* (PSA), a bacteria that can result in the death of kiwifruit vines. It is harvested in Northern Italy about 35 days before 'Hayward' which means the last week of September.

Fruits can be stored for 2-3 months at 0° C.

SUMMARY OF THE INVENTION

The present invention is a new and distinctive kiwifruit variety, designated 'Red Queen' Breeder's Reference: RK 2018. It was obtained during the course of a planned plant breeding program, which took place in the Emilia-Romagna region near Milan, Italy between 2008-2013. The 'Red Queen' variety was selected from a population of seedlings obtained from freely-pollinated 'RS1' fruits. About 450 seedlings of 'RS1' fruits were pollinated with various males, particularly 'Tomuri' and 'Chieftain' which both proved to be perfectly compatible with 'RS1'. 'Red Queen' first flowered in April 2011 and fruits were assessed in October 2011. All referenced dates are northern hemisphere timings.

In 2012, 'Red Queen' variety was grafted on 'Hayward' and 'Tomuri' rootstock, and the asexually reproduced plants proved to be true to type. The location where the first act of asexual reproduction took place is Castel Bolognese (Emilia Romagna) Italy.

In 2014, the first trial plot of plants grafted on both 'Hayward' and 'Tomuri' were established in Latina, Italy. The resulting first fruits harvested in 2016 proved to maintain the unique features observed in the nursery.

Germination period is 10-12 days before 'Hayward', which means about one week after 'RS1'. Flowering period is last week of April, means 10 days before 'Hayward' and one week after 'RS1'. Ripening period is last week of October, about 25 days after 'RS1'. Harvesting should be performed when the external pulp tends to lose its green color and starts to turn to yellow. The harvest date of the instant plant was Oct. 20, 2017 in Emilia Romagna (Northern Italy).

'Red Queen' is moderately vigorous and has close internodes. The germination percentage during spring is very high: 70-85%. The plant has a bushy growing habit and responds effectively to cuts of green pruning, generating a large number of offshoots. The 'Red Queen' variety presents panicles with a number of flowers ranging from 4 to a maximum of 7. The plant is malleable and responds very well to pruning. Production is uniform, with many single fruits, a few double fruits and a high share of USDA grade #1 fruits.

Fruits are oblong with a tendency to develop into a slightly pear shape, of variable length between 50-80 mm and width between 35-45 mm. The fruit's medial section is circular.

The peel has a green-brown 152D shade of color and is glabrous. The pulp is yellow 4B on the outside and red 44B in the center. The red 44B and yellow 4B color increases in uniformity after the 4th year of implantation and so does the overall ripening of fruits. The fruit's columella is cream-white 11D in color and of a medium-soft consistency, more consistent in proximity of the stalk.

The shelf life of 'Red Queen' is strongly dependent on the harvesting method, but is typically 4-5 months and, in ideal conditions, it can even reach 6 months.

Brix degrees at the time of consumption range from 19° to 21° with a medium level of acidity.

In the Table 1 and 2 descriptions, color references are made to The Royal Horticultural Society Color Chart, 2001, except where general terms of ordinary dictionary significance are used.

Distinctive characteristics of the variety include the following shown in Table 1:

| Number | Characteristics | State Expression |
|---|---|---|
| 1 | Plant: sex | Feminine |
| 2 | Plant: parthenocarpy | Absent |
| 3 | Plant: Vigour | Medium |
| 4 | Young shoot: hair density | Limited |
| 5 | Young shoot: anthocyanin coloration on the growth edge | Limited |
| 6 | Stalk: thickness | Medium |
| 7 | Stalk: offshoot color on the sun-exposed side | Brown 199A |
| 8 | Stalk: bark texture | Slightly coarse |
| 9 | Stalk: hair density | Light |
| 10 | Stalk: strength | Medium |
| 11 | Stalk: length | 50/70 cm |
| 12 | Stalk: diameter | 12/15 mm |
| 13 | Stalk: lenticels size | Small, 3-4 per square cm |

-continued

| Number | Characteristics | State Expression |
|---|---|---|
| 14 | Stalk: lenticels shape | Thin rectangular |
| 15 | Stalk: lenticels length | 3-4 mm |
| 16 | Stalk: lenticels number | Medium |
| 17 | Stalk: surface of the bud's base | Medium, almost smooth |
| 18 | Stalk: presence of pearls | Absent |
| 19 | Stalk: size of the pearl's orifice | Absent |
| 20 | Leaf callus | Concave |
| 21 | Stalk: fibrous part | Fibrous, watery |
| 22 | Leaf blade: shape | Mostly heart-shaped in the young age. It becomes orbiculate in the adult plant with a slightly dentate margin. Margin shows 3-4 spikes per linear cm. |
| 23 | Leaf blade: length/width ratio | 1:1. Average leaf width is 18-20 cm. Average length is 13-15 cm. |
| 24 | Leaf blade: tip's shape | Acuminate in adult age; shallow notch in a round apex in young age. |
| 25 | Leaf blade: basal lobes | Lightly overlapping |
| 26 | Leaf blade: number of ciliated indentations | Medium |
| 27 | Leaf blade: hair density in the upper part | Absent |
| 28 | Leaf blade: hair density in the lower part | Very sparse - subtle |
| 29 | Leaf blade: green intensity in the upper part | Intense green 134A |
| 30 | Leaf blade: color in the lower part | Light green 134C |
| 31 | Leaf blade: variegation | Absent |
| 32 | Leaf blade: variegation color | Absent |
| 33 | Leaf: stalk size and texture | Average length 12-15 cm, average diameter 3 mm, and smooth texture |
| 34 | Stalk: anthocyanin color in the upper part | Absent |
| 35 | Panicle: type | Raceme type with 4 to 7 single flowers. Sometimes double/triple flowers can appear. |
| 36 | Panicle: number of flowers | 4-7 |
| 37 | Flower bud: first bud position | Basal |
| 38 | Flower bud: shape | Mostly round |
| 39 | Flower bud: length | 3 mm |
| 40 | Flower bud: diameter | 4-6 mm |
| 41 | Flower bud: color | Light brown 199B |
| 42 | Flower: number of sepals | 6 or 7 |
| 43 | Flower: sepal color | 146D |
| 44 | Flower: sepal shape | Similar to an upside-down teaspoon. Apex is mostly round. |
| 45 | Flower: sepal consistency | Slightly fibrous |
| 46 | Flower: sepal texture | Margin is smooth. Smooth on the inner side and slightly hairy on the outer side. |
| 47 | Flower: density of sepal hairs | Medium |
| 48 | Flower: diameter and depth | Medium - 52 mm; 20 mm depth. |
| 49 | Flower: petal placement | Overlapping |
| 50 | Flower: profile shape | Flat |
| 51 | Flower: number of stigma | Medium - 30/35. |
| 52 | Flower: placement of stigma | Irregular |
| 53 | Petal: main color of the adaxial side | White-yellowish 155B |
| 54 | Petal: main color shade | 145B |
| 55 | Petal: secondary color on adaxial side | Green 145B |
| 56 | Petal: secondary color distribution | Almost absent |
| 57 | Petal: shape | Round. Apex mostly round, sometimes slightly acuminate. Margin irregular base: slightly acuminate. |

-continued

| Number | Characteristics | State Expression |
|---|---|---|
| 58 | Petal: texture | Velvety for both surfaces |
| 59 | Anther: color | Intense yellow 6A |
| 60 | Fruit: weight | Average weight: 85-90 gr |
| 61 | Fruit: length | 50-80 mm |
| 62 | Fruit: width | 35-45 mm |
| 63 | Fruit: length-width ratio | 1:1.7 |
| 64 | Fruit: shape | Oblong with a tendency to develop into a slightly pear shape |
| 65 | Fruit: shape in central section (approx. mid fruit) | Circular |
| 66 | Fruit: lower part | Lightly concave |
| 67 | Fruit: presence of sharp protuberance | Absent |
| 68 | Fruit: presence of ring at the calyx | Absent |
| 69 | Fruit: edge shape at stem end | Lightly rounded |
| 70 | Fruit: stem length | Long - 4-5 cm |
| 71 | Fruit: stem diameter | 2-3 mm |
| 72 | Fruit: stem length in relation to fruit length | Long |
| 73 | Fruit: presence of lenticels on skin | Limited - lenticel number is approximately 6/7 per square centimetres |
| 74 | Fruit: lenticel diameter | 2 mm |
| 75 | Fruit: lenticel height | 1 mm |
| 76 | Fruit: Absence of hair on skin | Hairs sparsely present |
| 77 | Fruit: hair density | Very sparse |
| 78 | Fruit: hair color | Light brown, almost absent |
| 79 | Fruit: hair adherence to skin | Strong |
| 80 | Fruit: skin color | Green-brown 152D, depending on light exposure |
| 81 | Fruit: hair adherence to pulp | Strong |
| 82 | Fruit: color of external pericarp | Greenish yellow 4B |
| 83 | Fruit: color of loculi-alveoli | Red 44B |
| 84 | Fruit: diffusion of red color around the loculi-alveoli (if present) | High |
| 85 | Fruit: intensity of the red color in the loculus | Strong |
| 86 | Fruit: extent of the columella in relation to the fruit | Medium |
| 87 | Fruit: overall shape of the columella in themid-section | Circular |
| 88 | Fruit: color of the columella | Cream white 11D |
| 89 | Fruit: sweetness | High |
| 90 | Faiit: acidity | Medium |
| 91 | Period of bud breakage | Medium-premature, approximately March 5. |
| 92 | Period of flowering | Averagely premature, approximately April 22. |
| 93 | Period of ripening for harvesting | Averagely tardive - approximately October 20. |

The typical and observed plan height at age 3 is about 4 meters, plant growth covers about 6-7 sqm., trunk texture is smooth, and trunk color is 177A.

The new variety can be asexually reproduced, both by promoting roots on cuts, using warm beds, or more conveniently through grafting on selected rootstocks. Plants grafted on male rootstocks proved to be more vigorous and more resistant than straight plants from cuts. Grafting can be operated within a wide window, from May into July. English single or double cut is the most common grafting technique. Trial plantings of grafted plants established in both Emilia Romagna (Castelbolognese) and Latina area in 2014 have shown that the unique combination of characteristics come true to form, are established, and transmitted through succeeding asexual propagations.

BRIEF DESCRIPTION OF THE DRAWINGS

Images show in the following identified pictures are from plants that are approximately four years from grafting.

The illustration on sheet 1 shows typical fruit of the new variety in the orchard.

Figure 3:
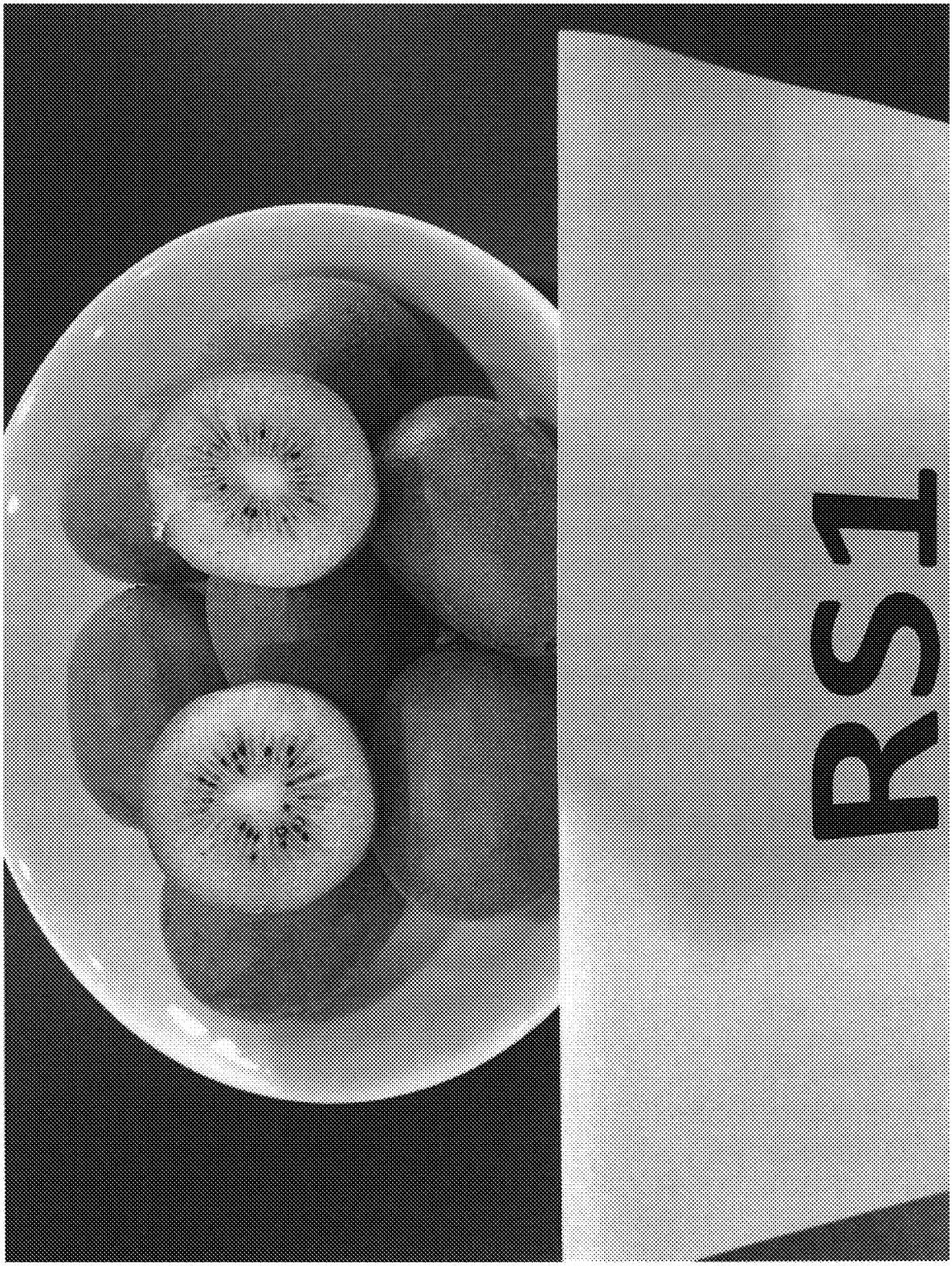

The illustration on sheet 2 shows closeup of typical fruit of the new variety in the orchard.

The illustration on sheet 3 shows typical fruit of the new variety in the orchard in cross-section, 10 days before harvest.

The illustration on sheet 4 shows a typical fruit of the new variety in the studio and in cross-section.

The illustration on sheet 5 shows a typical fruit of the new variety in the studio and on a scale.

The illustration on sheet 6 shows typical fruit of the parent female 'RS1' species in the studio, including in cross-section.

The illustration on sheet 7 shows typical fruit of the new variety in the studio compared with the parent female 'RS1' species, including in cross-section.

COMPARISON TO CLOSEST VARIETY

'Red Queen' variety shows some distinctive features common to 'RS1' varieties, such as a navel at the bottom, oblong shape with a tendency to develop into a slightly pear shape, hairless fruits and very high fertility.

Comparison with the similar variety 'RS1' (protected by CPVO Europe under the title # EU46694) shows that 'Red Queen' may be distinguished as follows in Table 2:

Comparison With Similar Variety.
Observations made under Italy Growing Conditions 2016-2019

| Characteristic | 'RS1' | 'Red Queen' |
|---|---|---|
| FRUIT: | | |
| Harvest date | Late September | Late October |
| Color of ripe pericarp | Bright yellow (44A)/ Bright red (44B) | Greenish yellow (4B) |
| Skin color | Greenish brown (152D) | Greenish brown (152D) |
| Mean fresh weight | 70-80 grams | 85-100 grams |
| Mean dry matter at harvest | 19-23% | 19-22% |
| Average length | 60 mm | 50-80 mm |
| Average width | 37 mm | 35-45 mm |
| Core diameter | 12 mm | 13 mm |
| Width/length ratio | 0.61 | 0.588 |
| Sweetness (Brix at maturity for consumption) | 20-22° | 19-21° |
| General shape | Oblong | Oblong with a tendency to develop into a slightly pear shape |
| Cross-sectional shape | Circular | Circular |
| Shape of stylar end | Navel | Navel |
| Skin: Hairness | Absent | Almost absent |
| VINE: | | |
| Shoots: | | |
| Color | 148A | 148A |
| Texture | Smooth | Smooth |
| Length | | 30-40 cm |
| Diameter | | 8-10 mm |

-continued

Comparison With Similar Variety.
Observations made under Italy Growing Conditions 2016-2019

| Characteristic | 'RS1' | 'Red Queen' |
|---|---|---|
| Stem: | | |
| Color (upper) | 165A | 166A |
| Color (lower) | 199A | 199A |
| Mean diameter | 9 mm | 9.5 mm |
| Texture | Smooth | Smooth |
| Lenticels (if present) | Present | Present |
| Length | | 40-50 mm |
| Lenticel number | | 6/7 per square centimetres |
| Diameter | | 2 mm |
| Height | | 1 mm |
| Leaf: | | |
| Color (upper) | 134A | 134A |
| Color (lower) | 134B | 134C |
| Venation color (upper) (mainly central vein only) | | 11B |
| Venation color (lower) | | 11A |
| Shape | Orbiculate | Heart-shaped in young age; orbiculate in adult age |
| Length | 120 mm | 130 mm |
| Width | 115 mm | 120 mm |
| Apex | Acuminate | Acuminate in adult age; shallow notch in round apex in young age |
| Base | Cordate | Cordate |
| Margin | Ciliate | Ciliate |
| Texture | Smooth | Smooth |
| Venation Pattern | | Reticulate |
| FLOWER: | | |
| Inflorescence: | | |
| Predominant number of flowers | 5-6 | 4-7 |
| Petiole: | | |
| Length | 100-105 mm | 105-115 mm |
| Color | 162A | 162B |
| Length | 35 mm | 37 mm |
| Color | 135C | 135C |
| Hairs | Smooth | Smooth |
| Length of hairs | | 12-15 cm |
| Diameter | | 3 mm |
| Texture | | Smooth |
| Flower: | | |
| Coloration of petals | Bi-colored | Bi-colored |
| Primary color | 155A | 155B |
| Secondary color | 145A | 145B |
| Petal shape | | Round |
| Petal apex | | Mostly round, sometimes slightly acuminate |

-continued

Comparison With Similar Variety.
Observations made under Italy Growing Conditions 2016-2019

| Characteristic | 'RS1' | 'Red Queen' |
|---|---|---|
| Petal margin | | Irregular |
| Petal base | | Slightly acuminate |
| Petal texture | | Velvety for both surfaces |
| Base of petals diameter | 48 mm | 50 mm |
| Arrangement of petals | Overlapping | Overlapping |
| Mean number of petals/flowers | 5-6 | 6 |
| Mean length of petals | 24 mm | 26 mm |
| Mean width of petals | 21 mm | 22 mm |
| Petal ratio of length/width | 1.15 | 1.17 |
| Petal shoulder | Present | Very pronounced |
| Filament color | 157A | 157A |
| Anther color | 6A | 6A |
| Attitude of styles | Erect | Erect |
| Curvature of styles | Absent | Absent |
| Color of styles | 157A | 157C |
| Amount of hair on ovary | Dense | Dense |
| Color of ovary | 157A | 157A |
| Shape of ovary | | Roundish |
| Diameter of ovary | | Appx 6 mm |
| Sepals: | | |
| Number of sepals | 6-7 | 6-7 |
| Color of sepals | 146C | 146D |
| Length | 8.5-11.0 mm | 9.3-11.5 mm |
| Mean length | 10.0 mm | 10.3 mm |
| Sepals diameter | 6.7 mm | 7.0 mm |
| Flower opening | Mid-April | Late April |
| Vegetative bud break | Mid-March | Early March |
| Plant/fruit disease and pest resistance | None | None |
| Plant hardiness zone or heat/cold resistance | Unknown | Unknown |

The most striking differences between 'RS1' and 'Red Queen' are the fruit shape ('RS1' is more pear-shaped, while 'Red Queen' is more oblong with a tendency to develop into a slightly pear shape) and size, flowering and harvest times, and storability. The fruit size is significantly bigger than 'RS1', and the biggest fruits on 'Red Queen' are obtained on medium wood, while the 'RS1' needs larger, strong wood to reach decent size. The bud break and blooming of 'Red Queen' are both delayed by about 1 week beyond that of 'RS1'. Also, fruit storability or 'Red Queen' is much longer than that of 'RS1', typically 4-5 months for 'Red Queen' versus two months for 'RS1'.

The invention claimed is:

1. A new and distinct kiwi plant of the species *A. chinensis* Planch substantially as herein described and illustrated.

* * * * *

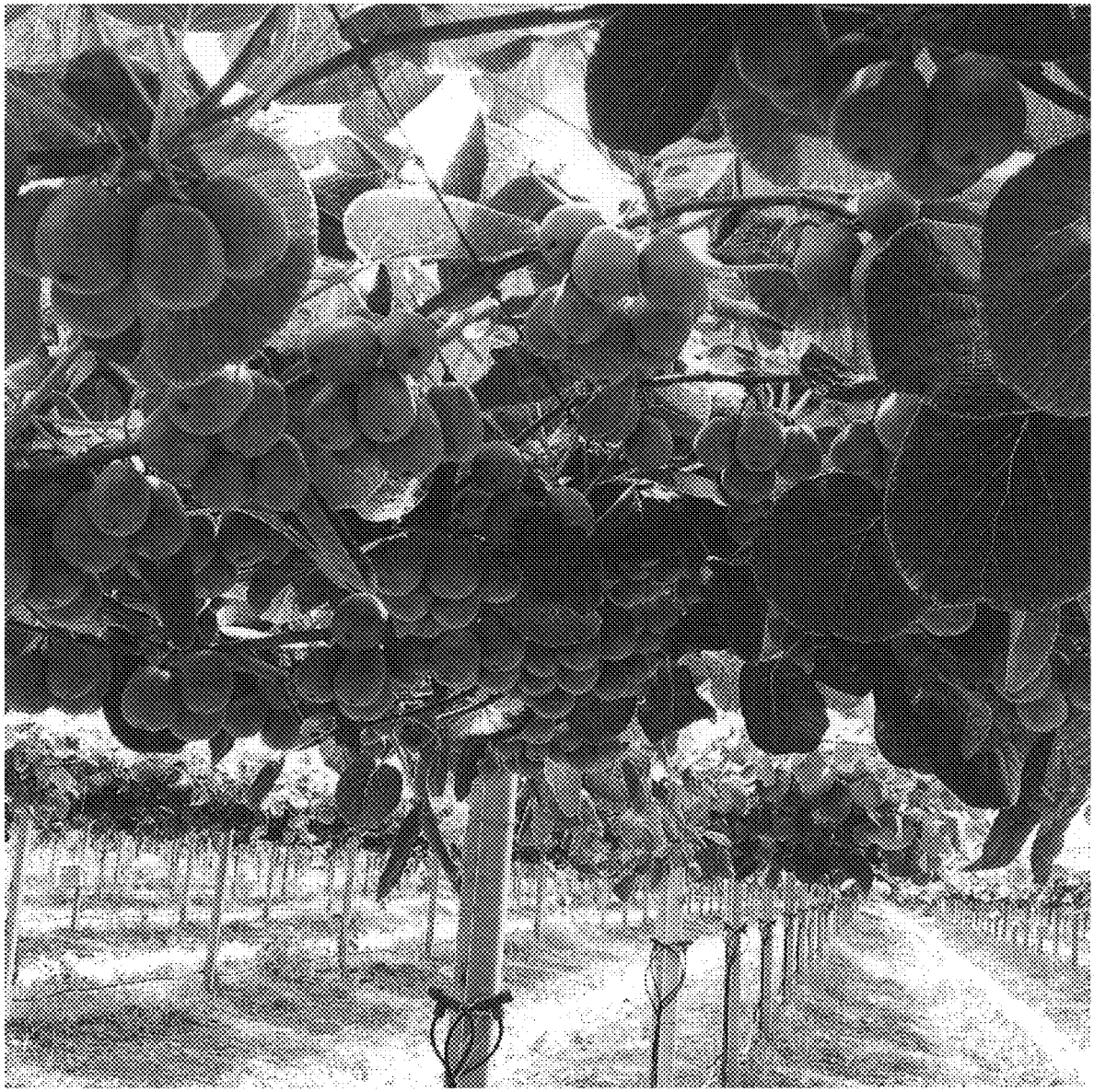

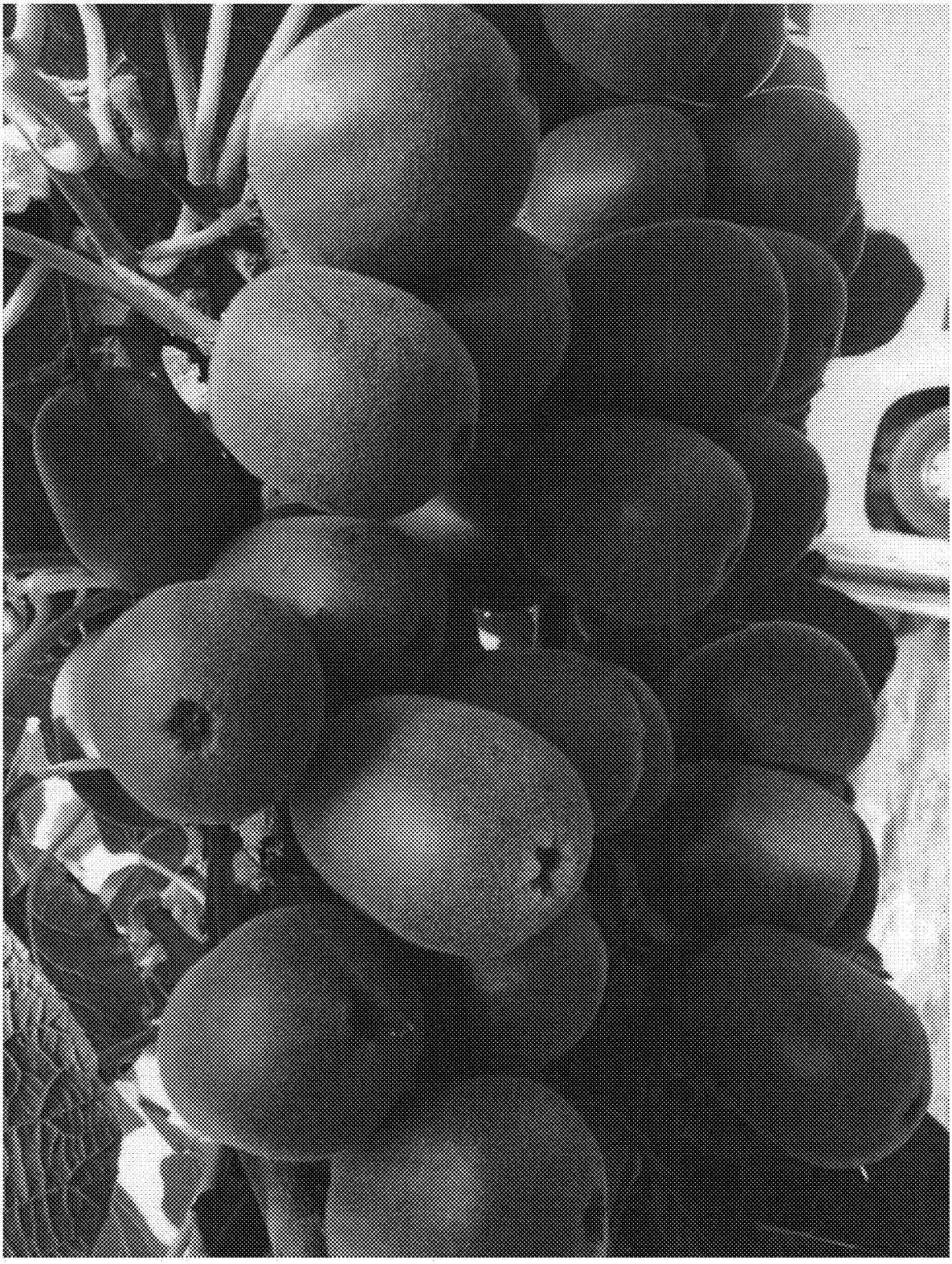

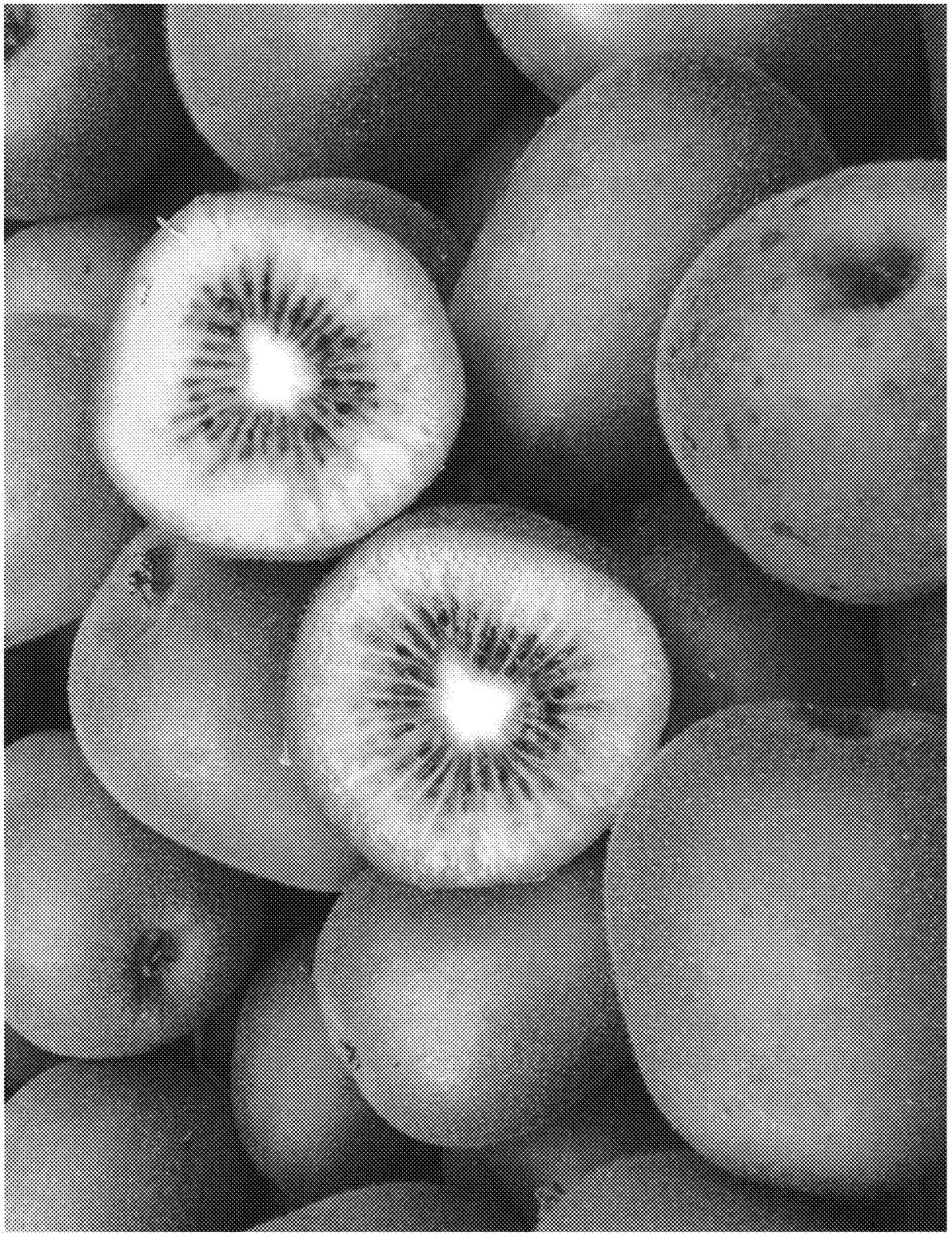

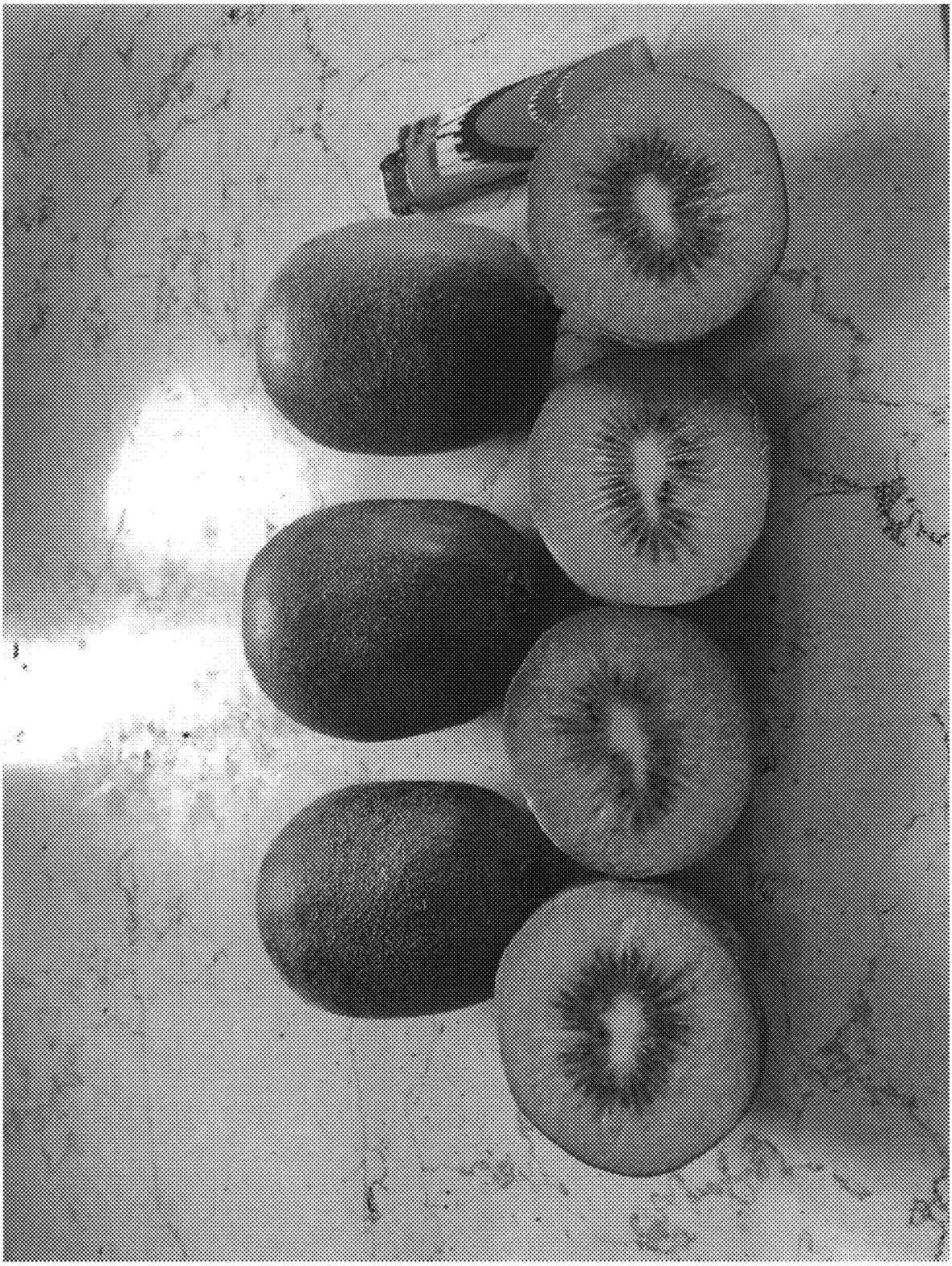

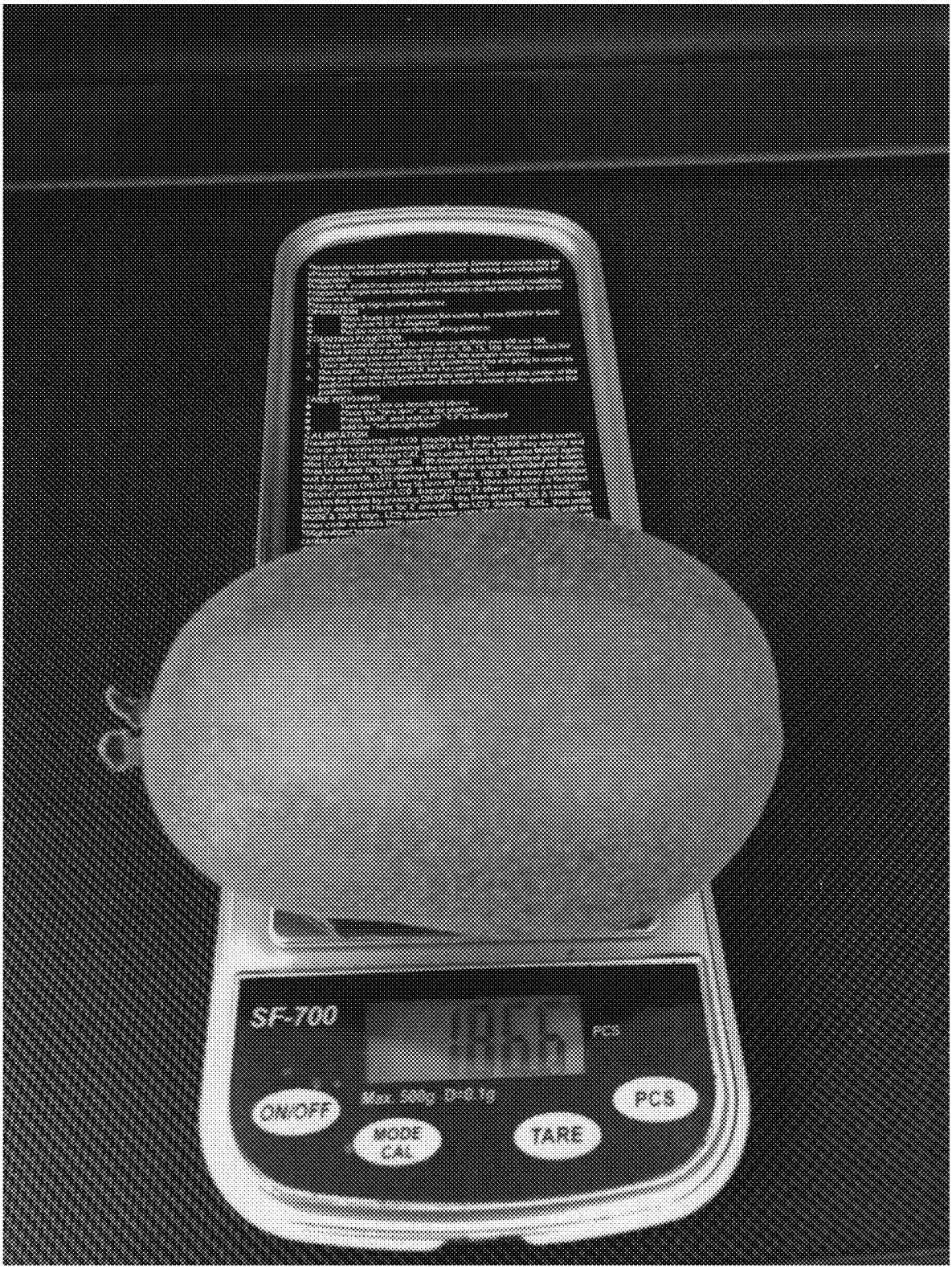
SF-700
ON/OFF
MODE
CAL
TARE
PCS

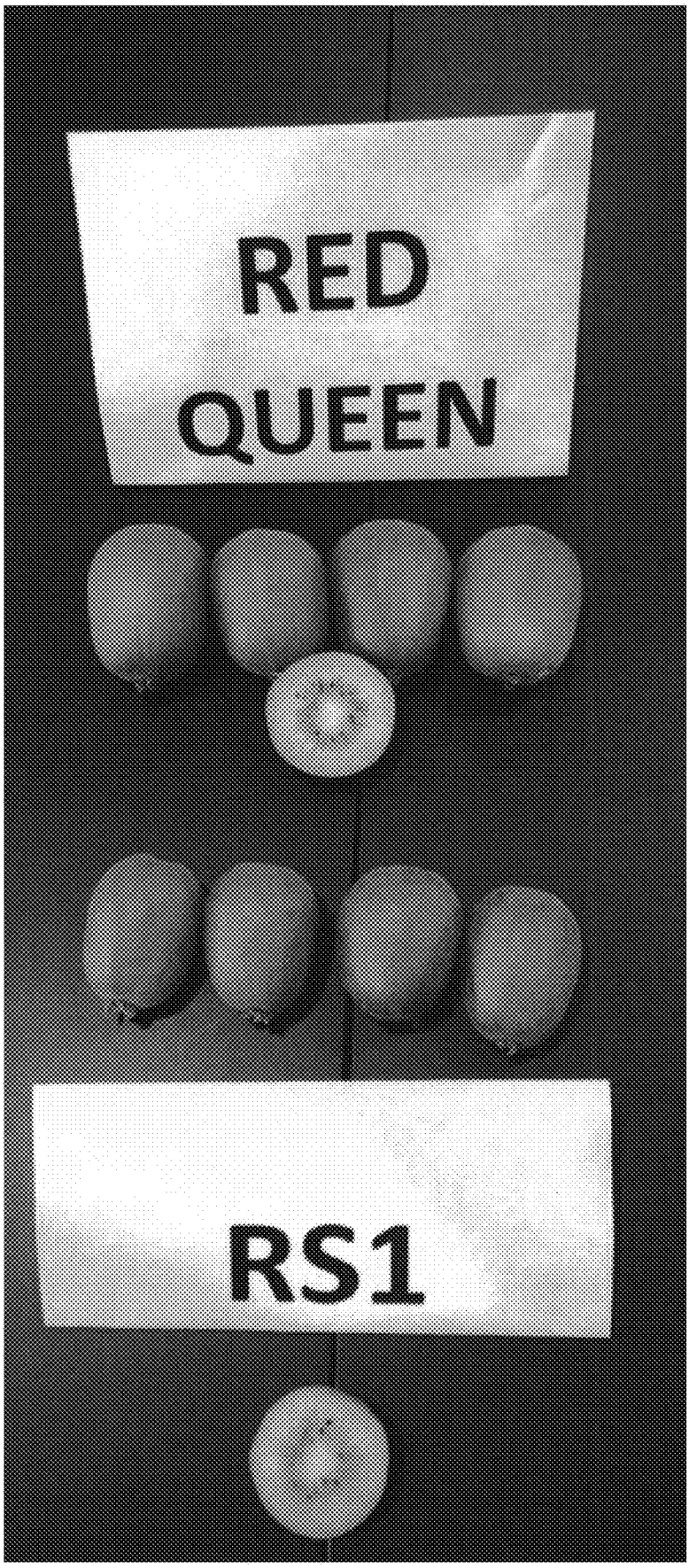
RED
QUEEN
RS1